US006153810A

United States Patent [19]

Huang et al.

[11] Patent Number: 6,153,810

[45] Date of Patent: Nov. 28, 2000

[54] HIGHLY SELECTIVE PROCESS FOR MAKING O-ARYLBENZONITRILES

[75] Inventors: Bao-Guo Huang, Cheektowaga; David Y. Tang, East Amherst, both of N.Y.

[73] Assignee: Occidental Chemical Corporation, Niagara Falls, N.Y.

[21] Appl. No.: 09/070,467

[22] Filed: Apr. 30, 1998

[51] Int. Cl.[7] .................................................. C07C 255/00

[52] U.S. Cl. .............................................................. 588/411

[58] Field of Search .............................................. 558/411

[56] References Cited

U.S. PATENT DOCUMENTS 5,240,928 8/1993 Allen et al. ............................. 514/259

FOREIGN PATENT DOCUMENTS 08231454 of 0000 Japan .

OTHER PUBLICATIONS

Danishefsky, S., et al, Selective Carbon–Carbon Bond Formation via Transition Metal Catalysis, 3. A Highly Selective Synthesis of Unsymetrical Biaryls and diarylmethanes by the Nickel–or Palladium–Catalyzed Reaction of Aryl–and Benzylzinc Derivatives, 1977.

*Primary Examiner*—Johann Richter
*Assistant Examiner*—Joseph Murray
*Attorney, Agent, or Firm*—Richard D. Fuerle; Anne E. Brookes

[57] ABSTRACT

Disclosed is a method of making an o-arylbenzonitrile by reacting o-chlorobenzonitrile with a substituted phenylzinc halide. The reaction is performed in the presence of a nickel catalyst, an ethereal solvent, and N-methylpyrrolidinone as a cosolvent.

20 Claims, No Drawings

HIGHLY SELECTIVE PROCESS FOR MAKING O-ARYLBENZONITRILES

BACKGROUND OF THE INVENTION

This invention relates to a process for making an o-aryl benzonitrile by reacting o-chlorobenzonitrile (OCBN) with a substituted phenylzinc halide. In particular, it relates to a method of making o-tolylbenzonitrile (OTBN) by reacting OCBN with p-tolylzinc chloride in the presence of a nickel catalyst, an ethereal solvent, and N-methylpyrrolidinone (NMP) as a cosolvent.

OTBN can be used as a building block in a new class of pharmaceutically active materials—the angiotensin-II-antagonists. A number of coupling approaches have been developed for making OTBN. For example, it can be made via direct coupling of aryl iodides under classical Ullman conditions. OTBN can also be made by reacting Grignard reagent with o-bromobenzonitrile (OBBN) or OCBN in the presence of a transition metal catalyst (Pd, Ni, or Mn). However, the high cost of raw materials, such as aryl iodide and OBBN, has limited the wide application of these methods.

The reaction of OBBN or OCBN with p-tolylboronic acid (Suzuki reaction) also gives a good yield of OTBN. This reaction performs well with an aryl bromide as an electrophile, but an expensive water soluble or bidentate ligand is required for the reaction of an aryl chloride. The reaction of OBBN with organozinc reagent (Neggish reaction) to make OTBN has also been tried.

SUMMARY OF THE INVENTION

We have discovered that OTBN and related o-arylbenzonitriles can be prepared by reacting OCBN with a substituted phenylzinc halide in the presence of a nickel catalyst, an ethereal solvent, and NMP as a cosolvent. While OCBN is less reactive than OBBN, we have nevertheless been able to obtain OTBN with an excellent yield (85 to 95%) using the method of this invention. In addition, the byproduct, 2,2'-dicyanobiphenyl, from homocoupling of OCBN, has been successfully eliminated under these conditions. The organozinc reagent is tolerant of a variety of functional groups and has less tendency to form homocoupling byproducts, which makes it more attractive.

DESCRIPTION OF THE PREFERRED EMBODIMENTS

In the process of this invention, OCBN is reacted with a substituted phenylzinc halide having the general formula:

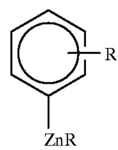

where R is alkyl or alkoxy from $C_1$ to $C_4$ and X is chlorine, bromine, or iodine. Preferably, R is alkyl, preferably methyl, and preferably R is in the para position because the products, such as OTBN, are commercially important. Also, X is preferably chlorine as that compound is easier to make. The preferred phenylzinc halide is p-phenylzinc chloride. The amount of phenylzinc halide should be about 1.0 to about 2.0 equivalents per equivalent of OCBN as less is ineffective and more is unnecessary; the preferred amount of phenylzinc halide is about 1.0 to about 1.2 equivalents.

About 0.5 to 10 mole % of a nickel catalyst is used in the reaction. Less catalyst is ineffective and more catalyst is unnecessary. The preferred amount of catalyst is about 2 to about 5 mole %, based on the weight of the OCBN. The catalyst has the general formula $NiL_mX'_n$, where the nickel is in the 0 or II oxidation state, L is an organic ligand bonded to the nickel atom, X' is chlorine, bromine, or iodine, m is 0 to 4, and n is 0 to 2; preferably, X' is chlorine, m is 2, n is 2, and L is triphenylphosphine as those catalysts are commercially available and, in some cases, those catalysts can be prepared in situ by reacting $NiX'_n$ with the organic ligand. Examples of ligands that can be used include triphenylphosphine, tricyclohexylphosphine, tributylphosphine, and acetylacetonate. Examples of suitable catalysts include dichlorobis(triphenylphosphine) nickel, $Ni(PPh_3)_2Cl_2$ (TPPN), where "Ph" is phenyl, dichlorobis(tributylphosphine)nickel, nickel(II) chloride and triphenylphosphine, nickel(II) chloride and tricyclohexylphosphine, nickel(II) acetylacetonate, tetrakis (triphenylphosphine)nickel(0), and tetrakis (triphenylphosphite)nickel(0). The preferred catalyst is TPPN because it has been found to work well and is readily available.

About 5 to about 30 mL per gram of OCBN of a solvent system, which comprises an ethereal solvent (i.e., a solvent that contains a C—O—C group) and NMP cosolvent, is used in the reaction. If less of the solvent system is used more unwanted byproducts may be produced and more of the solvent system is unnecessary. The preferred amount of combined ethereal solvent and NMP cosolvent is about 10 to 20 mL per gram of OCBN. Examples of suitable ethereal solvents include THF, methyl t-butylether (MTBE), hydroxyethyl acetate glycol monoacetate, diethyl ether, diethylene glycol diethyl ether, 1,2-dimethoxy ethane, diethylene glycol dimethyl ether, 1,2-bis(2-methoxyethoxy) ethane, bis[2-(2-methoxyethoxy)ethyl]ether, diethyleneglycol dimethyl ether, and diethylene glycol ether. The preferred ethereal solvent is THF because it has been found to work well. In the solvent system, about 2 to 12 molar equivalents of NMP should be used per equivalent of OCBN. Less NMP is ineffective and more NMP is unnecessary. Preferably, about 6 to about 8 equivalents of NMP should be used.

The reaction can be performed in various ways, but is preferably performed by adding the substituted phenylzinc halide to a mixture of the OCBN, the nickel catalyst, the solvent, and the NMP at temperatures of between 0 to about 25° C. for about 1 to about 10 hours. A temperature of about 0 to about 10° C. is preferred. The reaction is complete when OCBN is no longer detected by gas chromatography (GC).

The following examples further illustrate this invention.

EXAMPLE 1

A solution of o-chlorobenzonitrile (1.55 g, 11.30 mmol) and dichloro-bis(triphenyl)phosphine nickel (0.37 g, 0.56 mmol, 5 mol%) in NMP (15 mL) was placed in a three-necked, round-bottomed flask. P-tolylzinc chloride (13.50 mmol, 1.2 equiv.), prepared from the reaction of p-tolylmagnesium chloride (1.50M, 9.0 mL,) and anhydrous zinc chloride (2.03 g, 14.9 mmol) in THF (20 mL), was slowly added over about 30 min., while maintaining the temperature at 0° C. Stirring was continued at that temperature for 5 hours. An OTBN GC yield of 95.9% was obtained based on internal standard analysis (tridecane), while no 2,2'-dicyano biphenyl (OCBN homocoupling product) was detected.

EXAMPLE 2

Example 1 was repeated using 1.55 g (11.30 mmol) of o-chlorobenzonitrile, 0.37 g (5 mol %) of dichlorobis (triphenylphosphine)nickel, and p-tolylzinc chloride (12.43 mmol, 1.1 equiv.) in NMP (15 mL) at 10° C. A GC yield of 85.5% was obtained based on internal standard analysis (tridecane), while no 2,2'-dicyano biphenyl was detected.

EXAMPLE 3

Example 1 was repeated using 1.55 g (11.30 mmol) of o-chlorobenzonitrile, 0.37 g (5 mol %) of dichlorobis (triphenylphosphine)nickel, and p-tolylzinc chloride (13.5 mmol, 1.2 equiv.) in NMP (15 mL). A GC yield of 85.1% was obtained after 30 min. based on internal standard analysis (tridecane) with 0.45% of 2,2'-dicyano biphenyl.

EXAMPLE 4—Comparative

Example 1 was repeated using 1.55 g (11.30 mmol) of o-chlorobenzonitrile, 0.37 g (5 mol %) of dichlorobis (triphenylphosphine)nickel, and p-tolylzinc chloride (13.5 mmol, 1.2 equiv.) in THF (35 mL). A GC yield of 67% was obtained after 2 hours at room temperature based on internal standard analysis (tridecane) with 1.13% of 2,2'-dicyano biphenyl. This example shows that the yield drops significantly when NMP is not present.

We claim:

1. A method of making an o-arylbenzonitrile comprising (A) preparing a mixture of (1) o-chlorobenzonitrile;

(2) about 1.0 to about 2.0 equivalents per equivalent of said o-chlorobenzonitrile of a substituted phenylzinc halide having the general formula

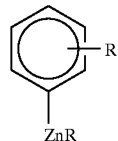

where R is alkyl or alkoxy from $C_1$ to $C_4$ and X is chlorine, bromine, or iodine;

(3) about 5 to about 30 mL per gram of said o-chlorobenzonitrile of a solvent system which comprises (a) an ethereal solvent; and (b) about 2 to 12 molar equivalents of N-methylpyrrolidinone per equivalent of said o-chlorobenzonitrile; and (4) about 0.5 to about 10 mole %, based on moles of said o-chlorobenzonitrile, of a nickel catalyst having the general formula $NiL_mX'_n$, where L is an organic ligand bonded to the nickel atom, X' is chlorine, bromine, or iodine, m is 0 to 4, and n is 0 to 2; and (B) reacting said o-chlorobenzonitrile with said substituted phenylzinc halide.

2. A method according to claim 1 wherein R is alkyl.

3. A method according to claim 2 wherein R is methyl.

4. A method according to claim 1 wherein R is in the para position.

5. A method according to claim 1 wherein X' is chlorine.

6. A method according to claim 1 wherein said substituted phenylzinc halide is p-tolylzinc chloride.

7. A method according to claim 1 wherein the nickel in said nickel catalyst is in the II oxidation state.

8. A method according to claim 1 wherein the nickel in said nickel catalyst is in the O oxidation state.

9. A method according to claim 1 wherein m is 2 and both L's are triphenylphosphine.

10. A method according to claim 1 wherein X is chlorine.

11. A method according to claim 10 wherein said catalyst is dichlorobis(triphenylphosphine)nickel.

12. A method according to claim 1 wherein said ethereal solvent is tetrahydrofuran.

13. A method of making an o-arylbenzonitrile comprising preparing a solution of (1) o-chlorobenzonitrile;

(2) about 2 to about 5 mole % of a nickel catalyst selected from the group consisting of dichlorobis (triphenylphosphine)nickel, dichlorobis (tributylphosphine)nickel, nickel(II) chloride and triphenylphosphine, nickel(II) chloride and tricyclohexylphosphine, nickel(II) acetylacetonate, tetrakis(triphenylphosphine)nickel(0), and tetrakis (triphenylphosphite)nickel(0); and (3) about 10 to about 20 mL per gram of o-chlorobenzonitrile of a solvent system which comprises (a) an ethereal solvent selected from the group consisting of tetrahydrofuran, methyl t-butylether, hydroxyethyl acetate glycol monoacetate, diethyl ether, diethylene glycol diethyl ether, 1,2-dimethoxy ethane, diethylene glycol dimethyl ether, 1,2-bis(2-methoxyethoxy) ethane, bis[2-(2-methoxyethoxy) ethyl]ether, diethyleneglycol dimethyl ether, and diethylene glycol ether; and (b) about 6 to about 8 equivalents of N-methylpyrrolidinone, per equivalent of said o-chlorobenzonitrile;

(B) mixing into said solution about 1.0 to about 1.2 equivalents per equivalent of said o-chlorobenzonitrile of a substituted phenylzinc chloride having the general formula

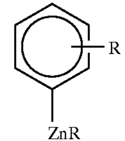

where R is alkyl or alkoxy from $C_1$ to $C_4$; and X is chlorine and (C) reacting said o-chlorobenzonitrile with said substituted phenylzinc chloride at a temperature of about 0 to about 25° C.

14. A method according to claim 13 wherein the nickel in said nickel catalyst is in the O oxidation state.

15. A method according to claim 13 wherein the nickel in said nickel catalyst is in the II oxidation state.

16. A method according to claim 13 wherein said nickel catalyst is dichlorobis(triphenylphosphine) nickel.

17. A method according to claim 13 wherein said substituted phenylzinc halide is p-tolylzinc chloride.

18. A method according to claim 13 wherein said ethereal solvent is tetrahydrofuran.

19. A method of making an o-tolylbenzonitrile comprising (A) preparing a solution of (1) o-chlorobenzonitrile;

(2) about 2 to about 5 mole % of dichlorobis (triphenylphosphine)nickel; and (3) about 10 to about 20 mL per gram of o-chlorobenzonitrile of a solvent system which comprises (a) tetrahydrofuran;

(b) and about 6 to about 8 equivalents of N-methylpyrrolidinone per equivalent of said o-chlorobenzonitrile; and (B) mixing into said solution about 1.0 to about 1.2 equivalents per equivalent of said o-chlorobenzonitrile of p-tolylzinc chloride; and (C) reacting said o-chlorobenzonitrile with said p-tolylzinc chloride at a temperature of about 0 to about 10° C.

20. A method according to claim 19 wherein said reaction is run for about 1 to about 10 hours.

* * * * *